US009347964B2

(12) United States Patent
Schacher (10) Patent No.: US 9,347,964 B2
(45) Date of Patent: May 24, 2016

(54) APPARATUS FOR SEPARATING CUVETTES

(71) Applicant: Roche Diagnostics Operations, Inc., Indianapolis, IN (US)

(72) Inventor: Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/508,606

(22) Filed: Oct. 7, 2014

(65) Prior Publication Data

US 2015/0104350 A1    Apr. 16, 2015

(30) Foreign Application Priority Data

Oct. 10, 2013    (EP) .................................... 13188200

(51) Int. Cl.
  *B65G 47/44*    (2006.01)
  *G01N 35/04*    (2006.01)
  *B65G 47/14*    (2006.01)

(52) U.S. Cl.
  CPC ............ *G01N 35/04* (2013.01); *B65G 47/1428* (2013.01); *B65G 2201/0235* (2013.01); *G01N 2035/0444* (2013.01); *G01N 2035/0456* (2013.01); *G01N 2035/0465* (2013.01)

(58) Field of Classification Search
  CPC ........... B65G 47/1428; B65G 47/1414; B65G 47/1457; B65G 47/1464; B65G 47/1492; B65G 47/1471; B65G 33/12; B65G 11/063
  USPC ......... 198/383, 389, 392, 396, 443, 658, 663; 193/10, 12
  See application file for complete search history.

(56) References Cited

U.S. PATENT DOCUMENTS

| | | | |
|---|---|---|---|
| 2,385,618 A | | 9/1945 | Ekstrand |
| 3,133,624 A | * | 5/1964 | Craig ......................... A61J 7/02 198/443 |
| 3,815,730 A | * | 6/1974 | Zwiep ................ B65G 47/1428 198/389 |
| 5,054,657 A | * | 10/1991 | Morse ....................... A47F 1/03 198/658 |
| 5,333,717 A | | 8/1994 | Rosenberg et al. |
| 5,765,676 A | * | 6/1998 | Kalm ................. B65G 47/1428 198/396 |
| 6,367,611 B1 | | 4/2002 | Kuenzler et al. |

FOREIGN PATENT DOCUMENTS

| | | |
|---|---|---|
| EP | 0567893 A1 | 11/1993 |
| EP | 1690813 A1 | 8/2006 |

* cited by examiner

*Primary Examiner* — William R Harp
(74) *Attorney, Agent, or Firm* — Roche Diagnostics Operations, Inc.

(57) ABSTRACT

An apparatus, system for analyzing, and process for separating cuvettes supplied in bulk form are presented. The apparatus comprises a reservoir with an inlet for supplying cuvettes in bulk form to a reservoir space, a separator with an outlet for outputting separated cuvettes from a separator space communicating with the reservoir space, a reservoir spiral contained in the reservoir space to transport cuvettes to the separator space by rotating the reservoir spiral, and a separator spiral contained in the separator space to transport cuvettes to the outlet by rotating the separator spiral. Adjacent turns of the separator spiral have an inter-distance dimensioned such that a cuvette can be held in a holding position in which projections projecting outwards from a body for receiving liquid rest on adjacent turns, with the body dipping into a spiral groove between the adjacent turns.

17 Claims, 7 Drawing Sheets

APPARATUS FOR SEPARATING CUVETTES

CROSS-REFERENCE TO RELATED APPLICATIONS

This application claims priority to EP 13188200.3, filed Oct. 10, 2013, which is hereby incorporated by reference.

BACKGROUND

The present disclosure generally relates to the field of biochemical research, biochemical routine analytics, clinical diagnostics and clinical research and relates to an apparatus for separating cuvettes supplied in bulk form. It further relates to a system for analyzing samples provided with an apparatus for separating cuvettes and a corresponding process for separating cuvettes supplied in bulk form to the system for analyzing samples.

In recent years, automated analytical instruments ("analyzers") offering a variety of analytical methods have become commercially available. Modern analyzers usually can process samples in standard sample vessels such as plastic cuvettes which allow for an easy and cost-effective sample analysis such as, for example, by photometric methods. In order to process samples in a batch-wise or continuous manner, it is known to supply a plurality of cuvettes in bulk form to the analyzer which, however, must be automatically separated for the processing of samples.

Therefore, there is a need to provide an apparatus for separating cuvettes which is simple and robust in construction, can be manufactured and maintained in cost-efficient manner and requires only small constructional space.

SUMMARY

According to the present disclosure, an apparatus for separating cuvettes supplied in bulk form. The apparatus comprises a reservoir with an inlet for supplying cuvettes in bulk form to a reservoir space; a separator with an outlet for outputting separated cuvettes from a separator space in communication with the reservoir space; a reservoir spiral contained in the reservoir space configured to transport cuvettes to the separator space by rotating the reservoir spiral; and a separator spiral contained in the separator space configured to transport cuvettes to the outlet by rotating the separator spiral. Adjacent turns of the separator spiral have an inter-distance dimensioned such that a cuvette is held in a holding position in which projections projecting outwards from a body for receiving liquid rest on adjacent turns, with the body dipping into a spiral groove between the adjacent turns Accordingly, it is a feature of the embodiments of the present disclosure to provide an apparatus for separating cuvettes which is simple and robust in construction, can be manufactured and maintained in cost-efficient manner and requires only small constructional space. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The term "cuvette" can be used to indicate a vessel comprising a body at least in part optically transparent to receive liquids in an inner space and to allow the photometric measurement of a liquid sample contained therein, i.e., the measurement of changes in optical transmission, such as absorbance and scattering, used in the optical analysis of analytes present in a sample. The cuvette may, for example, be used in the performance of scattering assays to detect the result of a chemical or biological reaction or to monitor the progress of a chemical or biological reaction such as, for example, in a coagulation assay, agglutination assay and turbidimetric assay.

In one embodiment, the body of the cuvette can comprise side walls, a closed bottom and an upper opening for allowing liquids to be introduced in the inner space formed by the side walls and the closed bottom. For use with the claimed apparatus, the cuvette can comprise (in exemplary embodiment, two) projections oppositely arranged with respect to each other and projecting outwards from the body of a cuvette. The projections can, for example, be arranged in proximity to the upper opening. In one embodiment, the cuvette can comprise two symmetrical projections arranged in opposite relationship with respect to each other. In one embodiment, the cuvette can have two plane-parallel walls wherein each wall can be provided with the projection projecting from the wall. In one embodiment, the cuvette can have a first pair of two plane-parallel walls and a second pair of two walls, wherein each wall of the first pair can be provided with the projection and the second pair of walls can be configured in such a manner that each cuvette can only have one orientation with respect to the separator spiral in which the projections can rest on adjacent turns of the separator spiral. In one embodiment, the walls of the second pair can have a shape that is different from the shape of the walls of the first pair, wherein the walls of the second pair can be shaped in such a manner that each cuvette can only have one orientation with respect to the separator spiral in which the projections can rest on adjacent turns of the separator spiral. In one embodiment, each wall of the second pair can have a width that is larger than a width of a wall of the first pair, with the width of a wall being given by a dimension perpendicular to the height of a cuvette, wherein the walls of the second pair can be dimensioned in such a manner that each cuvette can only have one orientation with respect to the separator spiral in which the projections can rest on adjacent turns of the separator spiral. In one embodiment, the projections can project perpendicularly from the body. In one embodiment, each projection can be integrally formed with the wall. The cuvette can, for example, be manufactured in one piece by injection molding polymeric material. In one embodiment, the volume can be below approximately 1 mL and can be adapted to receive a volume of liquid below about 0.5 mL. In one embodiment, the body can comprise side walls and two openings to allow liquid to flow through. The cuvette may thus be embodied as a channel, tube or capillary flow-through vessel. The cuvette may have an inner volume in the milliliter or microliter range. The various embodiments of the cuvette can be used alone or in any combination thereof.

As used herein, the term "bulk form" can describe a disordered state of a plurality of cuvettes, for example, present in a cluster. Cuvettes in bulk form can be separated (individualized) to be delivered separately for the processing of samples.

A new apparatus for separating cuvettes supplied in bulk form, e.g. to an analytical system or instrument, is proposed. In one embodiment, the apparatus for separating cuvettes can comprise a first (hollow) container, in the following denoted as "reservoir", having a first wall, in the following denoted as "reservoir wall" forming a first hollow space, in the following denoted as "reservoir space", with the reservoir wall provided with an opening serving as inlet for supplying cuvettes in bulk form to the reservoir space. The first container can serve as reservoir for storing cuvettes.

In one embodiment, the apparatus can comprise a second (hollow) container, in the following denoted as "separator", having a second wall, in the following denoted as "separator wall", forming a second hollow space, in the following denoted as "separator space", with the reservoir and separator configured in such a manner that the reservoir space can communicate with the separator space so that cuvettes can be transported from the reservoir space to the separator space. In one embodiment, the separator wall can be provided with an opening serving as outlet for delivering separated cuvettes such as, for example, for processing samples in an analytical system.

In one embodiment, the reservoir can comprise an axially symmetric first spiral, in the following denoted as "reservoir spiral", arranged in the reservoir space which can (directly or indirectly) be rotated around a rotational axis as given by a central spiral axis (symmetry axis). In one embodiment, the reservoir spiral can be arranged adjacent the reservoir wall. In one embodiment, the reservoir spiral can be arranged on (in contact with) the reservoir wall. In one embodiment, the reservoir spiral can be integrally formed with the reservoir wall forming the reservoir space.

Specifically, in one embodiment, the reservoir can be a rotatable reservoir, with a rotational axis of the reservoir identical to the spiral axis of the reservoir spiral, so that the reservoir spiral can be indirectly rotated by rotating the reservoir. In the latter case, the reservoir spiral can, e.g., be rotatably fixed with respect to the reservoir wall and can, e.g., be integrally formed with the reservoir wall which can facilitate manufacturing of the reservoir. In one embodiment, the reservoir spiral can be a directly rotatable spiral, i.e., the reservoir spiral can be directly rotated relative to the reservoir wall. In the latter case, the reservoir spiral can, e.g., be arranged to have a distance from the reservoir wall.

The reservoir spiral comprises plural spiral can turn extending to the outlet of the reservoir. Specifically, the reservoir spiral can transport cuvettes, e.g. in bulk form, towards the outlet by rotating the reservoir spiral. Accordingly, cuvettes can be transported from the reservoir space to the separator space by indirectly or directly rotating the reservoir spiral. In one embodiment, an inter-distance between adjacent turns of the reservoir spiral can be larger than an inter-distance between adjacent turns of the below-described separator spiral in order to transport cuvettes in bulk form towards the outlet. The size of the bulks can be reduced during the transport of the cuvettes towards the outlet of the reservoir.

In one embodiment, the separator can comprise an axially symmetric second spiral, in the following denoted as "separator spiral", arranged in the separator space which can be rotated around a rotational axis as given by a central spiral axis (symmetry axis). In one embodiment, the separator spiral can be adjacent the separator wall. In one embodiment, the separator spiral can be arranged on (in contact with) the separator wall. In one embodiment, the separator spiral can be integrally formed with the separator wall.

Specifically, in one embodiment, the separator can be a rotatable container rotatable around the spiral axis of the separator spiral so that the separator spiral can be indirectly rotated by rotating the separator. In that case, the separator spiral can, for example, be rotatably fixed with respect to the separator wall and can, for example, be integrally formed with the separator wall which facilitates manufacturing of the separator. In one embodiment, the separator spiral can be a directly rotatable spiral, i.e., the separator spiral can be directly rotated relative to the separator wall. In that case, the separator spiral can, for example, have a distance from the separator wall.

The separator spiral can comprise plural spiral turns extending to the outlet of the separator and can be adapted to transport cuvettes to the outlet by rotating the separator spiral. Furthermore, the separator spiral can hold cuvettes in a holding position in which the projections of a cuvette can rest on adjacent turns of the separator spiral, with the body dipping into a spiral groove between the adjacent spiral turns. Accordingly, cuvettes can be separated by the separator spiral by holding cuvettes in holding position. The separator spiral can thus serve for both separating cuvettes and transporting separated cuvettes in holding position to the outlet of the separator wherein rotation of the separator can facilitate threading up of cuvettes by the separator spiral. In one embodiment, the separator can comprise one or more entraining elements, such as, but not limited to, bars, for example, placed on the separator spiral, to entrain cuvettes when rotating the separator spiral so that cuvettes not in holding position in the separator space can be rearranged to facilitate threading-up by the separator spiral.

In one embodiment, the apparatus for separating cuvettes supplied in bulk form can comprise a reservoir with an inlet for supplying cuvettes in bulk form to a reservoir space, a separator with an outlet for outputting separated cuvettes from a separator space communicating with the reservoir space, a reservoir spiral contained in the reservoir space to transport cuvettes to the separator space by rotating the reservoir spiral, a separator spiral contained in the separator space to transport cuvettes to the outlet by rotating the separator spiral, wherein adjacent turns of the separator spiral can have an inter-distance dimensioned such that a cuvette can be held in a holding position in which projections projecting outwards from a body for receiving liquid can rest on adjacent turns, with the body dipping into a spiral groove between the adjacent turns.

Accordingly, the apparatus can be used to store cuvettes supplied in bulk form and to deliver cuvettes separately. The apparatus can be comparably simple and robust in construction so as to be suitable for long-term maintenance-free usage. Moreover, the apparatus can be highly compact in design resulting in a comparably small foot-print and comprises only few components enabling low-cost and easy production. As a result, the process of analyzing samples can be facilitated and performed in cost-efficient manner.

In one embodiment, the reservoir wall can be provided with a first opening serving as inlet for supplying cuvettes in bulk form to the reservoir space and a second opening for transporting cuvettes to the separator space, wherein the separator wall can be provided with a first opening for communication with the reservoir and a second opening serving as outlet for delivering separated cuvettes. Specifically, in one embodiment, the second opening (outlet) of the reservoir can be within the separator space so that cuvettes can readily be transported from the reservoir space to the separator space. In one embodiment, the second opening (outlet) of the reservoir can extend beyond the outlet of the separator. In one embodiment, the second opening (outlet) of the reservoir can be formed by an end portion of the reservoir which can be inserted through the first opening of the separator in order to position the second opening (outlet) of the reservoir in the separator space. In one embodiment, the end portion of the reservoir can taper conically towards the second opening (outlet) so that the end portion can readily be inserted through the first opening of the separator. This embodiment can enable a very compact construction of the apparatus of the invention.

In one embodiment, the apparatus can comprise at least one actuator coupled to the reservoir spiral and/or to the separator spiral for rotation. Specifically, the apparatus can, for example, comprise a first actuator coupled to the reservoir for rotating the reservoir and a second actuator coupled to the separator for rotating the separator, wherein the first and second actuators can be independently drivable from each other. Accordingly, the reservoir and separator can be rotated independently from each other so as to enable transport of cuvettes from the reservoir to the separator without delivering separated cuvettes or delivery of separated cuvettes without transporting cuvettes from the reservoir to the separator. Hence, operation of the apparatus can be adapted to the specific demands for analyzing samples. In one embodiment, the apparatus can comprise one actuator which can be coupled to the reservoir spiral and/or separator spiral for rotation. Specifically, the actuator can be coupled to the reservoir spiral and/or separator spiral by a speed increase gears or speed reduction gears so as to increase or decrease the rotational speed of the reservoir spiral and/or separator spiral, wherein in one embodiment, the reservoir spiral and separator spiral can be rotated by different rotational speeds. In one embodiment, one actuator can be coupled for rotation of the reservoir spiral and separator spiral can be decoupled from the reservoir spiral and/or separator spiral so as to rotate only the reservoir spiral or to rotate only the separator spiral. Coupling or decoupling can readily be reached, for example, by mechanical engagement.

In one embodiment, the separator spiral can be configured in such a manner that cuvettes can slide along the turns by the action of gravity when rotating the separator spiral. Accordingly, friction occurring between a cuvette (i.e. projections) and the spiral turns can be sufficiently low so that the cuvette can slide to the lowest point of the separator spiral by the mere action of gravity. As a result, cuvettes in holding position can be transported to the outlet without being rotated around the spiral axis of the separator spiral. Hence, cuvettes can be kept in holding position and reliably be transported to the separator outlet lined-up in a row between two adjacent turns of the separator spiral.

In one embodiment, the reservoir and/or separator can be made of electrically conductive material which, in an embodiment, can be connected to ground. Accordingly, electrostatic charging of cuvettes which often can be a problem in handling cuvettes can be advantageously avoided.

In one embodiment, the reservoir and the separator can be rotatably fixed to a mount by rollers which can enable an easy and quick fixation of the reservoir and separator, respectively. Furthermore, the reservoir and separator can readily be driven for rotation by the rollers in case at least one roller is a driven roller.

In one embodiment, the outlet of the separator can be connected to a chute for transporting cuvettes away from the separator. In one embodiment, the chute can comprise a decelerator, capable of decelerating cuvettes when entering the chute and/or when sliding along the chute.

In one embodiment, the separator can comprise a shield arranged between the outlet of the reservoir and the outlet of the separator. Specifically, the shield can be arranged in such a manner that a clearance can be present between the shield and the separator spiral which can be dimensioned such that only a cuvette in holding position can pass the clearance so that cuvettes not in holding position are blocked by the shield. Accordingly, the shield can prevent cuvettes not in holding position from being transported to the outlet of the separator.

In one embodiment, the apparatus can comprise a feed hopper connected to the inlet of the reservoir for feeding cuvettes in bulk form to the reservoir space. Accordingly, a large number of cuvettes can be stored so as to increase the time between re-fills of the apparatus.

In one embodiment, an inter-distance between adjacent turns of the separator spiral can be dimensioned such that only one cuvette or only one row of single cuvettes lined-up one after the other between adjacent turns can be placed between the adjacent turns of the separator spiral only in a specific orientation in which cuvette walls provided with the projections face the adjacent turns. Accordingly, threading up of cuvettes by the separator spiral can be facilitated.

In one embodiment, the separator spiral can have an end portion for delivering separated cuvettes to the outlet of the separator, which, for example, can be configured as a slide. The slide can, for example, be coupled to a chute for transporting cuvettes away from the outlet. In one embodiment, the outlet can comprise a cuvette gate configured to hold or release cuvettes depending on an angular position of the outlet with respect to the chute. Specifically, in one embodiment, the gate can be pretensioned in a closed position so that delivery of separated cuvettes can be blocked in case the outlet is positioned away from the chute. The cuvette gate can be opened by contact with the chute when the separator is rotated thereby allowing delivery of separated cuvettes from the slide to the chute when the outlet is aligned with the chute.

In one embodiment, the apparatus can comprise a controller for separating cuvettes supplied in bulk form and delivering separated cuvettes. In one embodiment, the controller can be setup to rotate the reservoir for transporting cuvettes from the reservoir space to the separator space in case no cuvette is contained in the separator space or a filling degree as given by the number of cuvettes contained in the separator is below a specifiable minimum filling degree. Accordingly, it can be ensured that the separator contains at any time a sufficient number of separated cuvettes ready to be delivered to the analytical system. A sensor such as, but not limited to, an optical sensor, gravimetric sensor or ultrasonic sensor, can be used to determine the cuvette filling degree of the separator so as to transport cuvettes from the reservoir to the separator in case the cuvette filling degree is lower than a specifiable cuvette filling degree.

In one embodiment, the controller can be setup to rotate the separator in a manner to adapt a rate of delivered separated cuvettes to a specifiable demand of cuvettes for analyzing samples. Accordingly, time and costs in sample processing can advantageously be saved.

A new system (or instrument) for analyzing samples is also presented. The system can comprise an apparatus for separating cuvettes supplied in bulk form according to one or more of the above embodiments. The system may further comprise a plurality of cuvettes as above-described. The system can be configured to analyze samples with respect to one or more analytical methods, such as, but not limited to, photometric methods, in particular photometric measurement in cuvettes. In one embodiment, the system can comprise a gripper for bringing cuvettes away from the outlet of the separator. In one embodiment, the gripper can bring cuvettes away from the lowest position of a chute connected to the outlet.

A new process for separating cuvettes supplied in bulk form to a system (or instrument) for analyzing samples is proposed. The process can comprise supplying cuvettes in bulk form to a reservoir space of a reservoir; transporting cuvettes from the reservoir space to a separator space of a separator by rotating a reservoir spiral contained in the reservoir space; separating cuvettes in the separator space by threading up cuvettes in a holding position between adjacent turns of a separator spiral contained in the separator space; and transporting cuvettes in holding position to an outlet of the separator by rotating the separator spiral.

In one embodiment, the reservoir spiral can be indirectly rotated by rotating the reservoir. In one embodiment, the reservoir spiral can be directly rotated. In one embodiment, the separator spiral can be indirectly rotated by rotating the separator. In one embodiment, the separator spiral can be directly rotated.

In one embodiment, cuvettes can be transported from the reservoir to the separator if no cuvette is contained in the separator or if a cuvette filling degree of the separator as given by the number of cuvettes contained in the separator is below a specifiable minimum filling degree.

In one embodiment, the separator can be rotated in a manner to adapt a rate of delivered separated cuvettes to a specifiable demand of cuvettes for analyzing samples.

In one embodiment, cuvettes in holding position can slide into a lowest position of the separator spiral by the mere action of gravity when rotating the separator.

Figure 1:
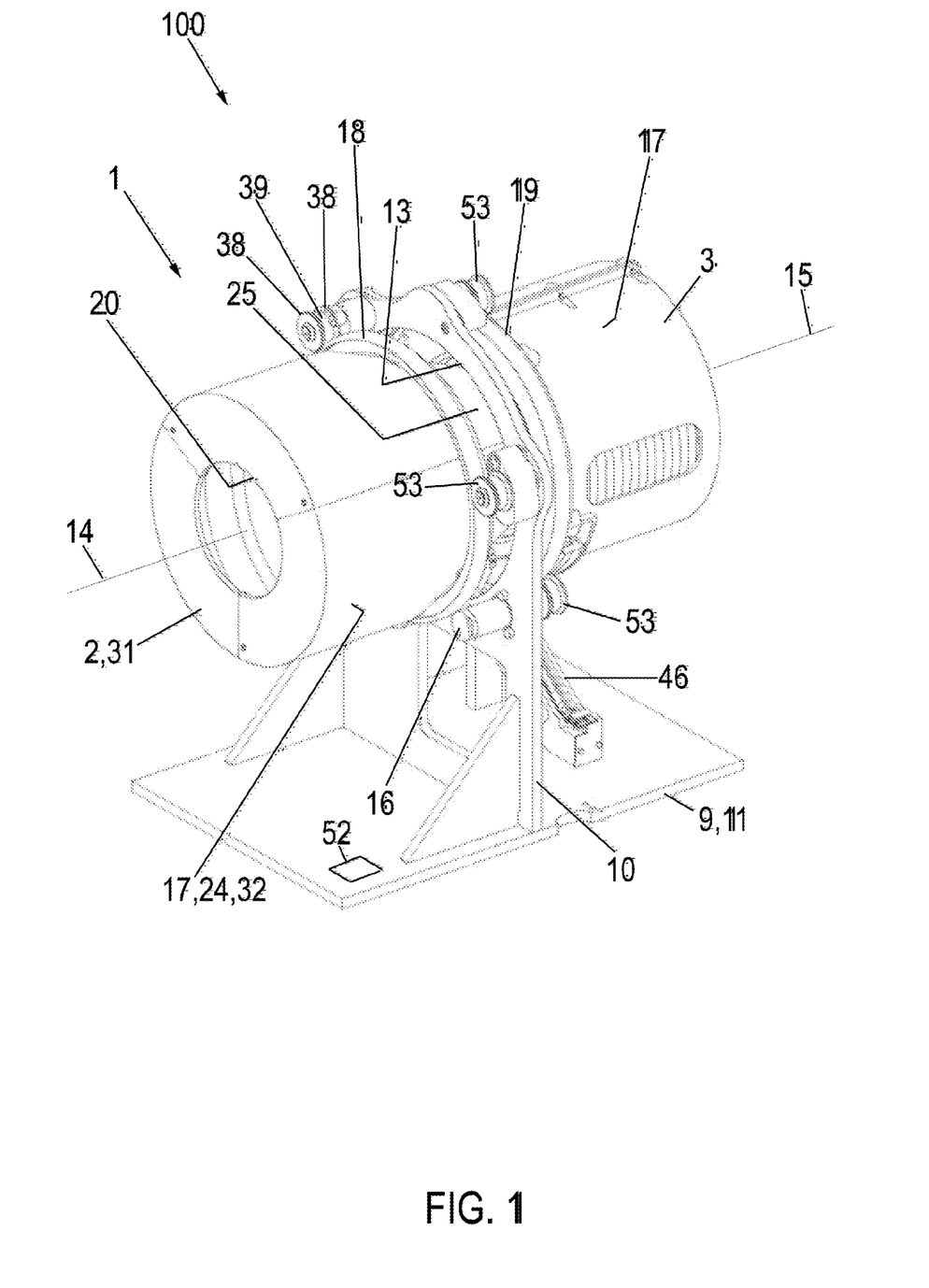
FIG. 1 illustrates a perspective view of an apparatus for separating cuvettes supplied in bulk form according to an embodiment of the present disclosure.

Referring initially to FIG. 1, an exemplary apparatus 1 for separating cuvettes is described. The apparatus 1 can, for example, be part of a system (or instrument) for processing samples, generally referred to as reference numeral 100, such as an analytical system (or instrument) for processing samples by one or more analytical methods such as, but not limited to, photometric methods.

Figure 2:
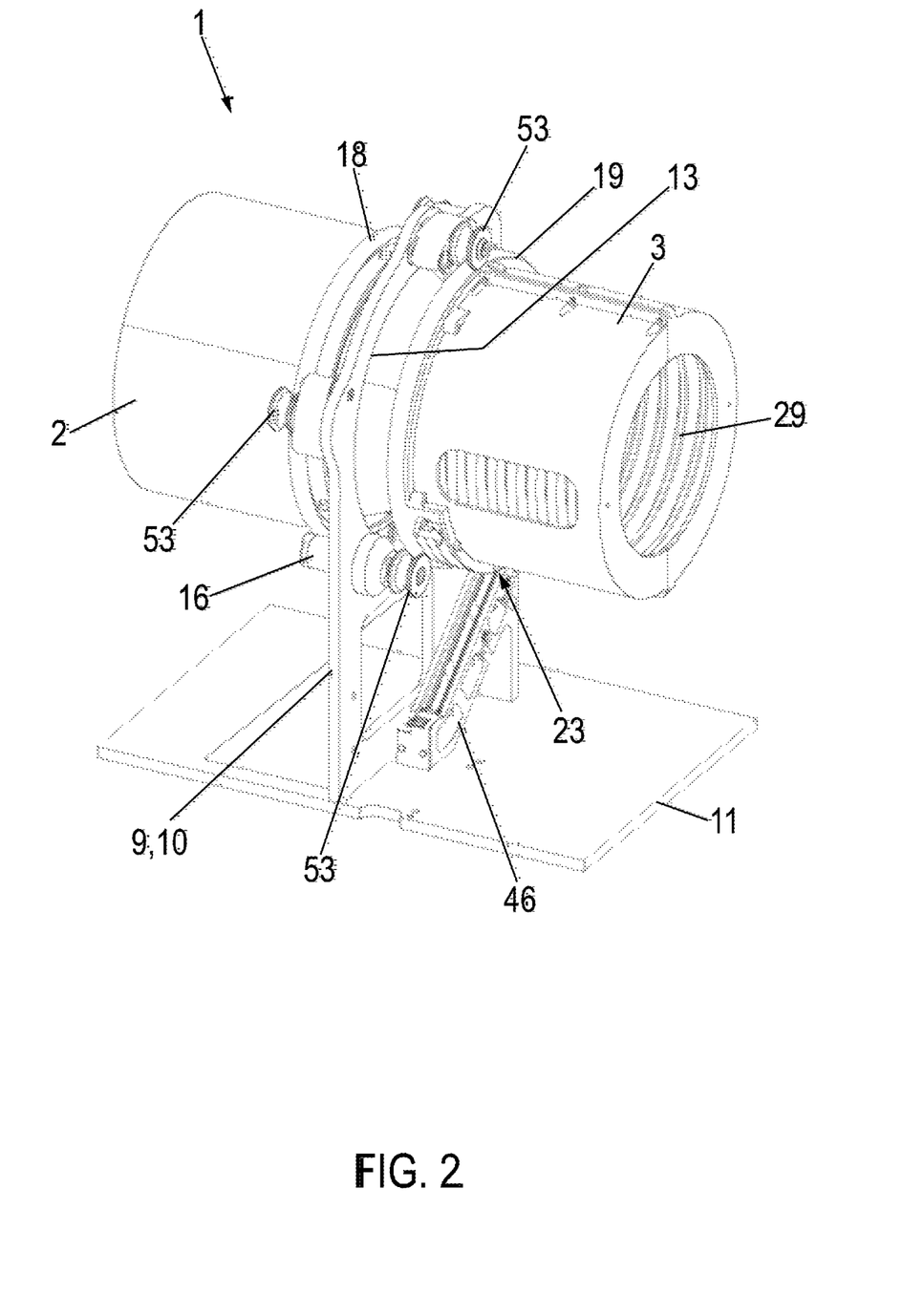
FIG. 2 illustrates another perspective view of the apparatus of FIG. 1 according to an embodiment of the present disclosure.
Figure 3:
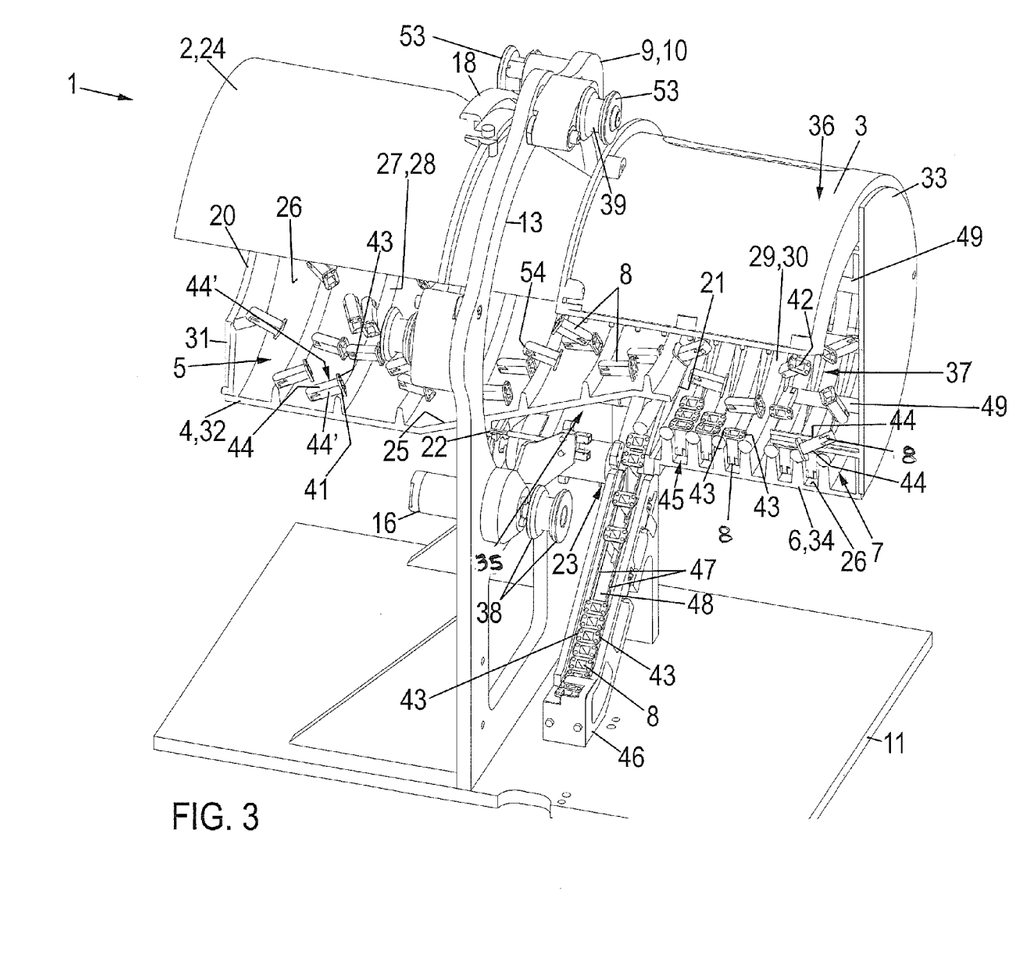
FIG. 3 illustrates a partially sectioned perspective view of the apparatus of FIG. 1 according to an embodiment of the present disclosure.

With particular reference to FIGS. 1-3, the apparatus 1 for separating cuvettes 8 can comprise two hollow containers, i.e., a reservoir 2 for storing cuvettes 8 and a separator 3 for separating cuvettes 8, both of which can be rotatably mounted to a mount 9. Specifically, the reservoir 2 can be rotated around a rotational axis as given by the symmetry axis, denoted as "reservoir axis 14", and the separator 3 can be rotated around a rotational axis as given by the symmetry axis, denoted as "separator axis 15". In the embodiment shown, the reservoir axis 14 and the separator axis 15 can be identical, but can also be different. As illustrated, both the reservoir 2 and separator 3 can, for example, be hollow drums. Both the reservoir 2 and the separator 3 are made of electrically conducting material such as, but not limited to, stainless steel, and are connected to electric ground (not further detailed) in order to prevent electrostatic charging of the cuvettes 8.

Specifically, the reservoir 2 and the separator 3 can be mounted to the opposite sides of a vertical mount plate 10 fixed in upright positions to a horizontal base plate 11. An upper portion of the mount plate 10 can be provided with a mount plate hole 13 (through-hole), with a plurality of rollers 53 arranged on each side of the mount plate 10 for rotatably fixing and rotating the reservoir 2 and separator 3, respectively. Specifically, a number of such as, for example, three, rollers 53 can be circumferentially arranged around the mount plate hole 13 on the reservoir 2-side of the mount plate 10 for mounting of the reservoir 2 and a number of, for example, three, rollers 53 can be circumferentially arranged around the mount plate hole 13 on the separator a-side of the mount plate 10 for mounting of the separator 3. For that purpose, each roller 53 can be provided with two rim-like roller crowns 38 having a small inter-distance so as to form a recessed roller track 39 between the roller crowns 38.

The reservoir 2 can comprise a first reservoir portion 24 cylindrical in shape and a conically tapering second reservoir portion 25. In a middle region of the reservoir 2 where the first reservoir portion 24 adjoins to the second reservoir portion 25, an outer surface 17 of the reservoir 2 can be provided with a protruding reservoir fixing ring 18 for mounting of the reservoir 2 to the mount 9. Specifically, the reservoir 2 can be rotatably fixed to the mount plate 10 by inserting the reservoir fixing ring 18 into the roller tracks 39 of the rollers 53 arranged on the reservoir 2-side of the mount plate 10. Similarly, an outer surface 17 of the separator 3 can be provided with a protruding separator fixing ring 19 so that the separator 3 can be rotatably fixed to the mount plate 10 by inserting the separator fixing ring 19 into the roller tracks 39 of the rollers 53 arranged on the separator 3-side of the mount plate 10. In order to obtain a secure rotatable fixation of the reservoir 2 and separator 3, respectively, a minimum number of three rollers 53, for example, having equal angular distances (for example, about 120°), can be arranged on each side of the mount plate 10. Those of skill in the art can appreciate that a larger number of rollers 53 can also be envisaged on each side of the mount plate 10.

In one embodiment, one roller 53 on each side of the mount plate 10 can be rotatably coupled to an individual electric motor 16 so that the reservoir 2 and separator 3 can be rotated independently from each other. The remaining rollers 53 can be idle rollers. Those of skill in the art can appreciate that a different fixing mechanism and/or a different rotating mechanism can also be envisaged With particular reference to FIG. 3, the reservoir 2 can be provided with a reservoir wall 4 having an inner surface 26 which can form an internal reservoir space 5 for receiving a plurality of cuvettes 8 in disordered or bulk form. Likewise, the separator 3 can be provided with a separator wall 6 having an inner surface 26 which can form an internal separator space 7 for receiving cuvettes from the reservoir space 5. The reservoir 2 can be open on both front-sides. Specifically, opposite to the separator 3, the reservoir wall 4 can comprise a front-sided reservoir front wall 31 provided with a first reservoir opening 20 serving as inlet for supplying cuvettes 8 in disordered or bulk form to the reservoir space 5. On the separator 3-side, the reservoir wall 4 can further comprise a front-sided second reservoir opening 21 serving as outlet for supplying cuvettes to the separator space 7. The second reservoir opening 21 can be formed by an end portion of the conically shaped second reservoir portion 25, with the second reservoir portion 25 tapering towards the second reservoir opening 21.

On the reservoir 2-side, the separator 3 can be provided with a first separator opening 22 for inserting the conically shaped second reservoir portion 25. Specifically, the second reservoir portion 25 can pass through the mount plate hole 13 and can extend beyond the first separator opening 22 so that the reservoir space 5 can communicate with the separator space 7 via the second reservoir opening 21. As illustrated, the second reservoir opening 21 can end freely within the separator space 7 without having contact to the separator wall 6.

The separator 3 can comprise a first separator portion 35 extending from the first separator opening 22 to a second separator opening 23 serving as outlet for delivering separated cuvettes 8. The separator 3 can further comprise a second separator portion 36 extending from the second separator opening 23 to a front-sided separator front wall 33 located opposite to the reservoir 2. Both the first separator portion 35 and the second separator portion 36 can be cylindrical in shape. The separator fixing ring 19 can be located at a front-sided end portion of the first separator portion 35.

With continued reference to FIG. 3, the reservoir 2 can be provided with a rotational-symmetric reservoir spiral 27 protruding from the inner surface 26 of the reservoir wall 4. In one embodiment, the reservoir spiral 27 can be integrally formed with the reservoir wall 4. As illustrated, the reservoir spiral 27 can comprise plural reservoir spiral turns 28 extending from the first reservoir opening 20 to the second reservoir opening 21, with a spiral axis of the reservoir spiral 27 being identical to the reservoir axis 14. Accordingly, by rotating the reservoir 2 the reservoir spiral 27 can be rotated around the spiral axis. As a result, cuvettes 8 can be transported from the reservoir space 5 to the separator space 7 by rotating the reservoir 2, provided that the reservoir 2 is rotated in the "right direction", which can be the opposite direction relative to the winding direction of the reservoir spiral turns 28. Stated more particularly, in case the reservoir spiral turns 28 are wound in clockwise-direction from the first reservoir opening 20 to the second reservoir opening 21, the reservoir 2 may have to be rotated counter-clockwise so as to transport cuvettes 8 towards the second reservoir opening 21, and vice versa. Since an inter-distance between adjacent reservoir spiral turns 28 can be larger than the length of one cuvette 8 and larger than an inter-distance between adjacent separator spiral turns 30 of the separator spiral 29 described below, cuvettes 8 in the reservoir space 5 can be transported in disordered or bulk form to the second reservoir opening 21 by rotating the reservoir 2. Accordingly, cuvettes 8 supplied in bulk form via the first reservoir opening 20 to the reservoir space 5 can readily be transported to the separator space 7 by rotating the reservoir 2. When leaving the second reservoir opening 21, cuvettes 8 fall into the separator space 7 in a cuvette receiving region 37 extending from the second reservoir opening 21 to the front-sided separator front wall 33.

Figure 4:
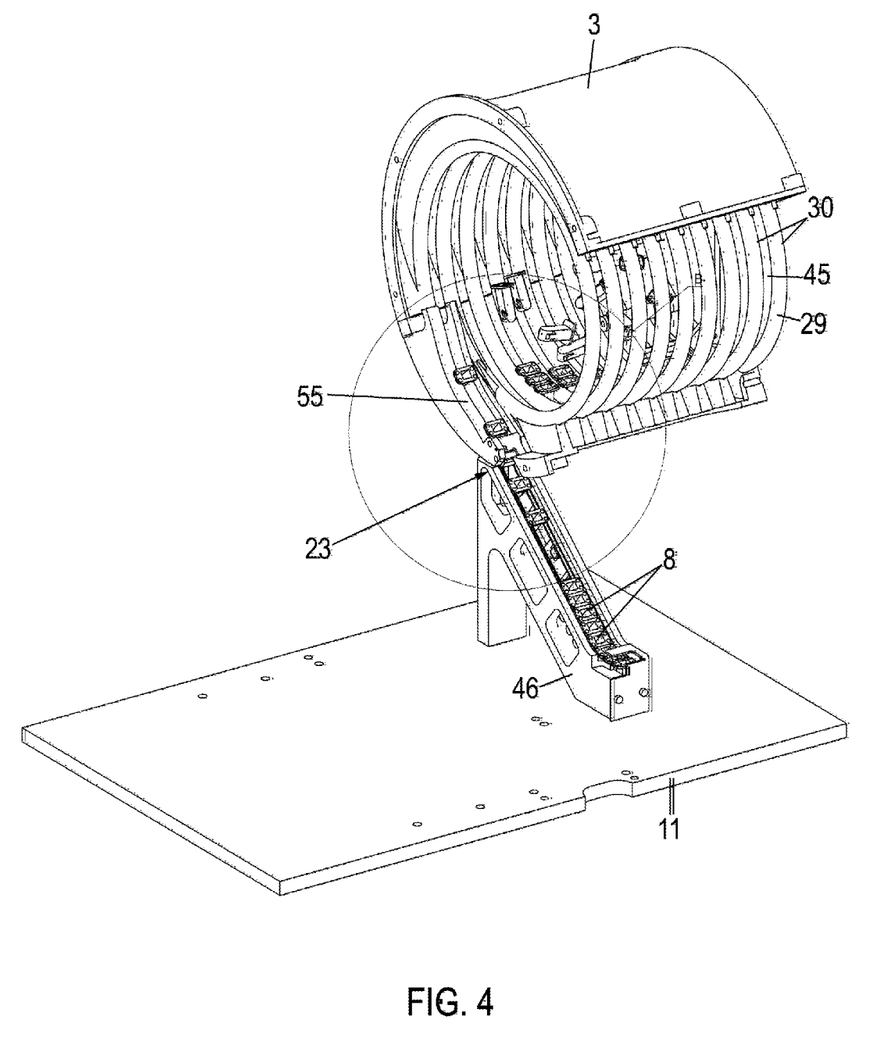
FIG. 4 illustrates a partially sectioned perspective view of the separator of the apparatus of FIG. 1 according to an embodiment of the present disclosure.
Figure 5:
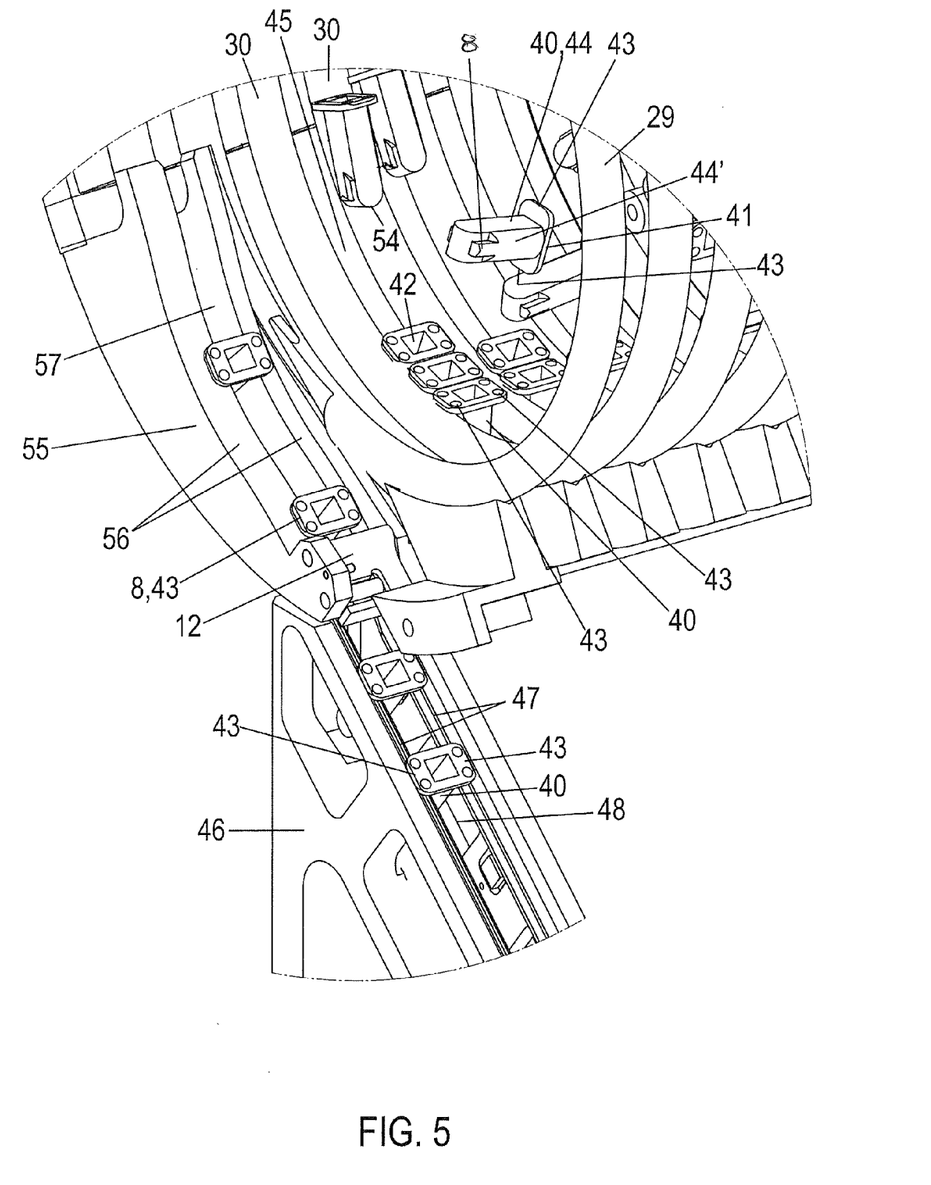
FIG. 5 illustrates a detail of FIG. 4 according to an embodiment of the present disclosure.

With yet continued reference to FIG. 3 and further reference to FIGS. 4 and 5, the separator 3 can be provided with a rotational-symmetric separator spiral 29 protruding from the inner surface 26 of the separator wall 6. In one embodiment, the separator spiral 29 can be integrally formed with the separator wall 6. The separator spiral 29 can comprise plural separator spiral turns 30 extending from the front-sided separator front wall 33 beyond the second reservoir opening 21 to the second separator opening 23 and, thus, can extend into the second separator portion 36. A spiral axis of the separator spiral 29 can be identical to the separator axis 15. Accordingly, by rotating the separator 3, the separator spiral 29 can be rotated around the spiral axis. As a result, by rotating the separator 3, cuvettes 8 in the cuvette receiving region 37 can be transported to the second separator opening 23 serving as outlet for separated cuvettes, provided that the separator 3 can be rotated in the "right direction" which can be the opposite direction relative to the winding direction of the separator spiral turns 30. Stated more particularly, in case the separator spiral turns 30 are wound in clockwise-direction from the front-sided separator front wall 33 to the second separator opening 23, the separator 3 may have to be rotated counter-clockwise so as to transport cuvettes 8 to the second separator opening 23, and vice versa.

The separator spiral 29 may not be only for transporting cuvettes 8 to the second separator opening 23 but also for separating (individualizing) cuvettes 8 as is more clearly explained in the following. As can be seen in FIG. 5, each cuvette 8 can comprise a body 40 having an inner space for receiving liquids. Generally, the body 40 can have a parallelepiped shape which, as illustrated, can be formed by two pairs of plane-parallel walls, i.e. a first pair of plane-parallel walls 44 and a second pair of walls 44', which in one embodiment can be plane-parallel walls 44'. Each cuvette 8 can be closed at the bottom 54 and open at the top-side at an upper cuvette opening 42. Furthermore, each cuvette 8 can have a flange 41 located adjacent the upper opening 42 and projecting (perpendicularly) outwards from the body 40. As illustrated, the flange 41 can comprise two opposing flange portions or projections 43 projecting from the first pair of plane-parallel walls 44. Each cuvette can be manufactured in one piece by injection moulding polymeric material so that both the flange 41 can be integrally formed with the body 40.

The separator spiral 29 can be adapted to the shape and size of the cuvettes 8. Stated more particularly, an inter-distance between adjacent separator spiral turns 30 can be dimensioned such that individual cuvettes 8 can be held in a holding position in which the projections 43 of a cuvette 8 rest on the adjacent separator spiral turns 30, with the body 40 dipping into a spiral groove 45 formed between the adjacent separator spiral turns 30. In holding position, the planes of the first pair of walls 44 can be perpendicularly oriented to the extension of the spiral groove 45, i.e. are facing the spiral turns 30. Accordingly, cuvettes 8 passing through the second reservoir opening 21 and falling into the cuvette receiving region 37 can likely be brought in holding position due to the rotation of the separator 3 which can cause a rearrangement of the disordered cuvettes 8. As a result, cuvettes 8 can be threaded up by the separator spiral 29 so that cuvettes 8 can be automatically separated. As additional measure, plural bars 49 can project circumferentially from the separator front wall 33 into the cuvette receiving region 37 for a certain distance over a few spiral turns 30 in order to facilitate threading-up of cuvettes 8. Stated more particularly, when the separator 3 is rotated, the bars 49 can entrain non-threaded-up cuvettes 8 in the cuvette receiving region 37 which can fall onto the spiral turns 30 when reaching a sufficiently high position thereby rearranging themselves and increasing the likeliness of being threaded-up between the spiral turns 30.

Furthermore, the inter-distance between adjacent separator spiral turns 30 can be dimensioned sufficiently small that only one cuvette 8 or a row of single cuvettes 8 lined up one after another can be threaded-up between two adjacent spiral turns 30, with the cuvettes 8 having a specific orientation in which the two opposing walls 44 provided with the projections 43 face the spiral turns 30 due to the fact that the other walls 44' have a width that is too large to fit into the spiral groove 45. Accordingly, cuvettes 8 can be hindered to be threaded up in an orientation different from the holding position and cuvettes 8 can be reliably threaded up in holding position by the separator spiral 29. Generally, one or a plurality of cuvettes 8 can be threaded up along one spiral groove 45. Then, by rotating the separator spiral 29 and separator 3, respectively, cuvettes 8 in holding position can be transported to the second separator opening 23.

Due to the fact that a friction occurring between the projections 43 and the adjacent separator spiral turns 30 of cuvettes 8 in holding position can be sufficiently low, threaded-up cuvettes 8 in holding position can slide along the separator spiral turns 30 to reach a lowest position of the separator spiral 29 with respect to gravity. Accordingly, when rotating the separator spiral 29, cuvettes 8 in holding position cannot be rotated with the separator spiral 29 and, thus, can reliably be kept in holding position during the transport to the second separator opening 23.

Figure 6:
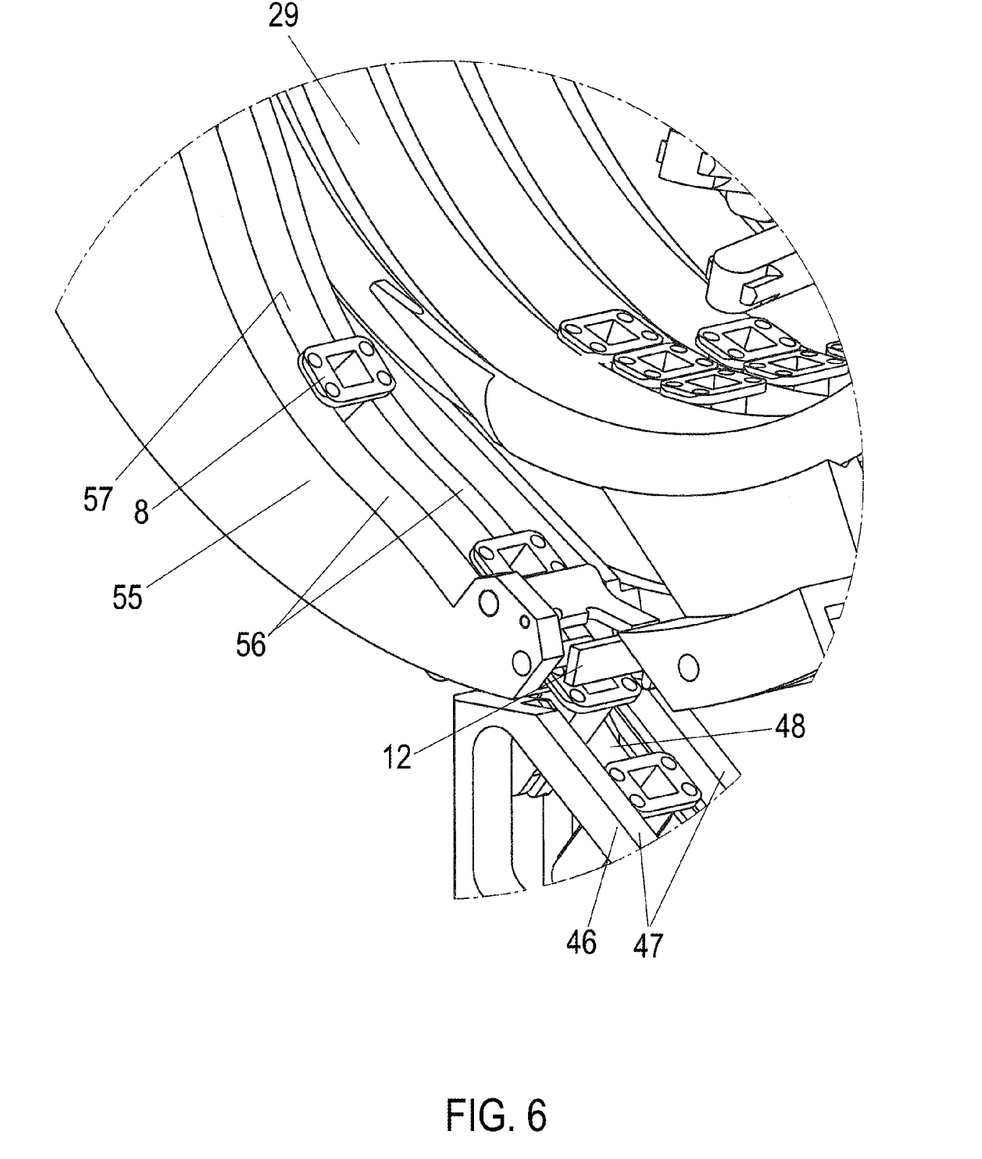
FIG. 6 illustrates an enlarged perspective view of the transition of the end portion of the separator spiral to the chute of the apparatus of FIG. 1 according to an embodiment of the present disclosure.

With particular reference to FIGS. 4-6, the end portion of the separator spiral 29 can be configured as slide 55. Stated more particularly, the last spiral turn 30 can extend to the slide 55 so that threaded-up cuvettes 8 transported to the last spiral turn 30 can be further transported to the slide 55, with the projections 43 of each cuvette 8 resting on two parallel slide rails 56 forming a slide groove 57 in-between for the cuvette body 40. Depending on the angular position of the separator 3, the slide 55 can be brought in a position in which it is continued by a downwards-oriented chute 46 having two parallel chute rails 47 for the projections 43 forming a chute groove 48 in-between for the cuvette body 40. Stated more particularly, as can best be seen in FIG. 5, the last separator spiral turn 30 adjacent the second separator opening 23 can pass over to the slide rails 56 which in a specific angular position of the separator 3 can pass over to the chute rails 47, with the spiral groove 45 continued by the slide groove 57 and, in one angular position of the separator 3, by the chute groove 48. Accordingly, cuvettes 8 in holding position transported to the second separator opening 23 can slide into and along the slide 55 and, in one angular position of the separator 3, can be transported to the chute 46, with the projections 43 resting on the slide rails 56 and the chute rails 47 and the body 40 dipping into the slide groove 57 and the chute groove 48. Accordingly, cuvettes 8 can readily be transported through and away from the cuvette outlet of the separator 3.

With particular reference to FIG. 6, in one embodiment, the apparatus 1 can comprise a cuvette gate, for example, configured as swivel plate 12, for blocking the slide 55 in a lower swivelled position (see FIG. 5) and releasing the slide 55 in an upper swivelled position (see FIG. 6). The swivel plate 12 can, for example, be operated by rotating the separator 3. Stated more particularly, in a specific angular position of the separator 3 in which the slide 55 continues to the chute 46, the swivel plate 12 can be brought in the upper swivelled position by level action of the upper part of the chute 46 upon rotation of the separator 3 so as to allow cuvettes 8 on the slide 55 to pass over to the chute 46. Otherwise, in case the slide 55 is rotated away from the chute 46, the swivel plate 12 can be resiliently brought in the lower swivelled position so as to hold cuvettes 8 on the slide 55 till the separator 3 is rotated to an angular position in which the slide 55 can be continued by the chute 46. In one embodiment, the slide rails 56 can broaden towards the chute 46 so that cuvettes 8 can dip deeper into the slide groove 57 in order to facilitate passing over to the chute 46. Accordingly, cuvettes 8 can controllably exit the separator 3 and be delivered from the slide 55 to the chute 46 only if the slide 55 is continued by the chute 46. The separator wall 6 can typically have a through-hole in correspondence to the slide groove 57, through which the cuvette body can slide.

As a result, cuvettes 8 supplied in bulk form to the reservoir 2 via the first reservoir opening 20 (cuvette inlet) can be transported to the separator 3 by rotating the reservoir 2 and, then, can be separated and transported to the second separator opening 23 (cuvette outlet) by rotating the separator 3. Generally, the reservoir 2 and separator 3 can be rotated independently from each other and, in particular, can be rotated in a same rotating direction or different rotating directions and with a same rotating speed or different rotating speeds, depending, for example, on the internal spiral configurations.

Figure 7:
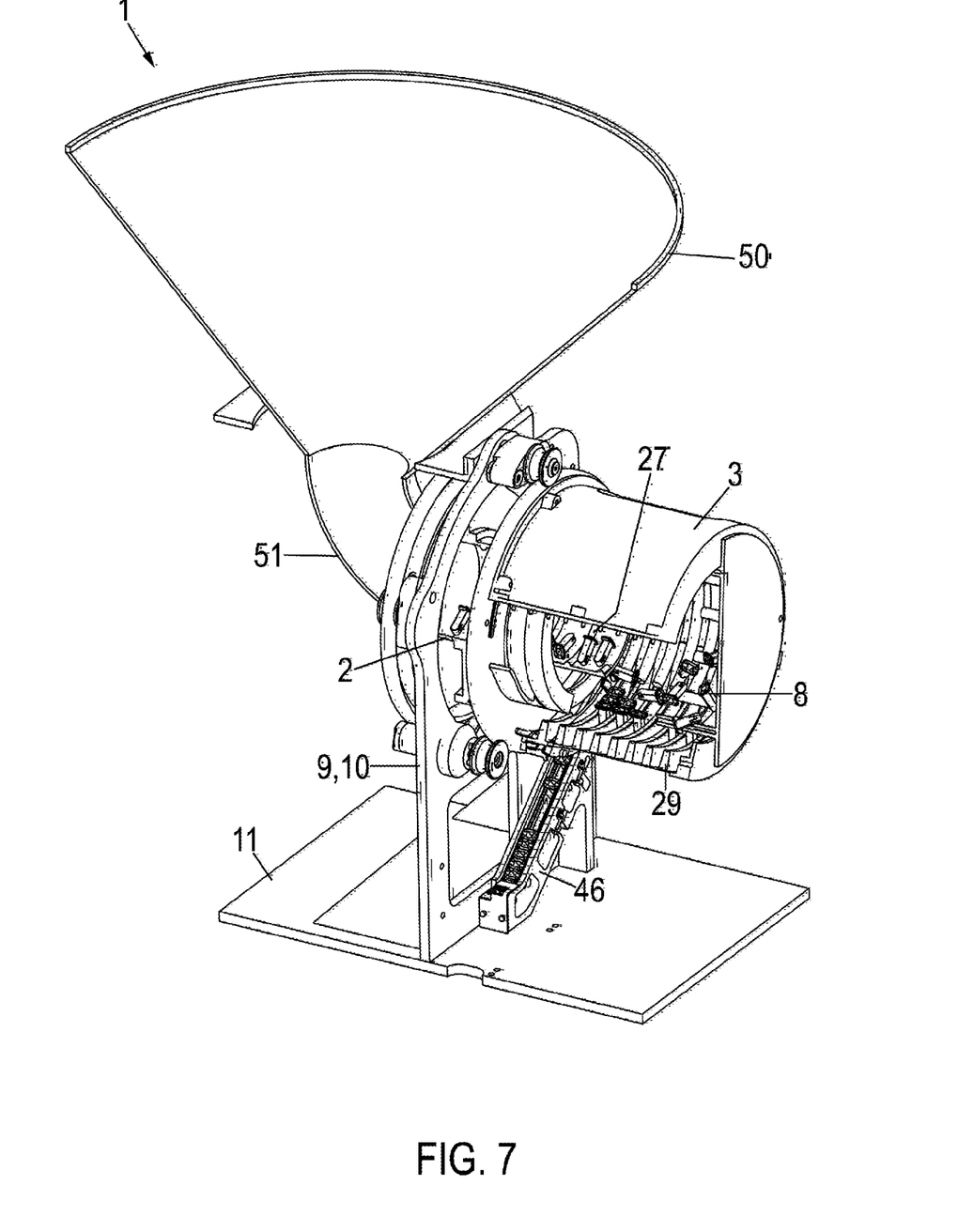
FIG. 7 illustrates a partially sectioned perspective view of a variant of the apparatus of FIG. 1 according to an embodiment of the present disclosure.

With particular reference to FIG. 7, a variant of the apparatus of FIG. 1 is presented. In order to avoid unnecessary repetitions, only the differences with respect to the embodiment of FIG. 1 are discussed and, otherwise, reference is made to the description of the above embodiment. Accordingly, the apparatus 1 can comprise a feed hopper 50 connected to the reservoir 2 via a curved fitting 51. As illustrated, the reservoir 2 can be configured as cylindrical container inserted into the separator space 7. By use of the feed hopper 50, a comparably large number of cuvettes 8 can be fed in bulk form to the reservoir 2 so that the time to re-fill cuvettes 8 can be prolonged.

As schematically illustrated in FIG. 1, in one embodiment, the apparatus 1 can comprise a controller 52 setup to control separation of cuvettes 8 supplied in bulk form. Specifically, the controller 52 can be setup to rotate the reservoir 2 and separator 3 to obtain separated cuvettes 8 at the cuvette outlet. Stated more particularly, in one embodiment, the controller 52 can be setup to rotate the reservoir 2 to transport cuvettes from the reservoir 2 to the separator 3 only in case no cuvette 8 is contained in the separator 3 or a cuvette filling degree of the separator 3 as given by the number of cuvettes 8 contained in the separator 3 is below a specifiable minimum filling degree. In one embodiment, the controller 52 can be setup to rotate the separator 3 to obtain a number of separated cuvettes 8 according to a specifiable demand for analyzing samples.

A system 100 for analyzing samples can comprise an apparatus 1 for separating cuvettes 8 supplied in bulk form and can also comprise cuvettes 8.

Obviously many modifications and variations can be possible in light of the above description. For instance, the rollers 53 of both sides of the mount plate 10 can be coupled to one (common) electric motor for rotation. In this case the reservoir 2 and separator 3 can be rotated together. In another variation, the reservoir axis 14 can be inclined with respect to the separator axis 15, in particular, to have an upwards direction towards the separator 3 which can help reduce the size of bulks of cuvettes 8 during transport to the separator 3 so as to facilitate the separation of cuvettes 8 supplied in bulk form.

Accordingly, the apparatus 1 can have many advantages over the prior art. A major advantage can be given by the fact that the apparatus 1 can be highly compact in design resulting in a comparably small foot-print, and simple and robust in construction so as to be suitable for long-term maintenance-free usage. It can comprise only few components enabling low-cost and easy production and small tolerances due to the small number of components. Samples can be processed in a highly cost-efficient manner.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. An apparatus for separating cuvettes supplied in bulk form, wherein each cuvette comprises a body having side walls, a closed bottom and an upper opening, the apparatus comprising:
 a reservoir with an inlet for supplying cuvettes in bulk form to a reservoir space;
 a separator with an outlet for outputting separated cuvettes from a separator space in communication with the reservoir space;
 a reservoir spiral contained in the reservoir space configured to transport cuvettes to the separator space by rotating the reservoir spiral; and
 a separator spiral contained in the separator space configured to transport cuvettes to the outlet by rotating the separator spiral, wherein adjacent turns of the separator spiral have an inter-distance dimensioned such that a cuvette is held in a holding position in which projections projecting outwards from a body of the cuvette for receiving liquid rest on adjacent turns, with the body dipping into a spiral groove between the adjacent turns.

2. The apparatus according to claim 1, wherein the reservoir is a rotatable reservoir.

3. The apparatus according to claim 2, wherein the reservoir spiral is integrally formed with a reservoir wall forming the reservoir space.

4. The apparatus according to claim 1, wherein the separator is a rotatable separator.

5. The apparatus according to claim 4, wherein the separator spiral is integrally formed with a separator wall forming the separator space.

6. The apparatus according to claim 1, further comprising, at least one actuator coupled to the reservoir spiral and/or to the separator spiral for rotation.

7. The apparatus according to claim 6, further comprising, at least one first actuator coupled to the reservoir for rotating the reservoir, and at least one second actuator coupled to the separator for rotating the separator, wherein the first and second actuators are independently drivable from each other.

8. The apparatus according to claim 1, wherein the separator spiral is configured in such a manner that cuvettes slide along the turns by the action of gravity when rotating the separator spiral.

9. The apparatus according to claim 1, wherein the reservoir comprises an outlet for transporting cuvettes to the separator space with the outlet arranged within the separator space.

10. The apparatus according to claim 1, wherein the reservoir and/or the separator are made of electrically conductive material.

11. The apparatus according to claim 1, further comprising, a feed hopper connected to the inlet of the reservoir for feeding cuvettes in bulk form to the reservoir space.

12. The apparatus according to claim 1, wherein an inter-distance between adjacent turns of the separator spiral is dimensioned such that only one cuvette or only one row of single cuvettes can be placed between the adjacent turns of the separator spiral only in an orientation in which cuvette walls provided with the projections face the adjacent turns.

13. The apparatus according to claim 1, wherein one or more entraining elements configured to entrain cuvettes when rotating the separator spiral are contained in the separator space.

14. The apparatus according to claim 1, wherein an end portion of the separator spiral is configured as slide for delivering separated cuvettes to the separator outlet, with the slide coupled to a chute for transporting cuvettes away from the outlet.

15. The apparatus according to claim 14, wherein the separator outlet comprises a cuvette gate configured to block or allow release of cuvettes from the separator outlet depending on an angular position of the separator outlet with respect to the chute.

16. The apparatus according to claim 1, further comprising, a controller setup to rotate the reservoir for transporting cuvettes from the reservoir space to the separator space in case no cuvette is contained in the separator space or a filling degree as given by the number of cuvettes contained in the separator is below a specifiable minimum filling degree, and/or to rotate the separator in a manner to adapt a rate of delivered separated cuvettes to a specifiable demand of cuvettes for analyzing samples.

17. A system for analyzing samples comprising an apparatus for separating cuvettes according to claim 1.

* * * * *